United States Patent [19]

Ts'o et al.

[11] 4,130,641
[45] Dec. 19, 1978

[54] INDUCTION OF INTERFERON PRODUCTION BY MODIFIED NUCLEIC ACID COMPLEXES

[76] Inventors: Paul O. P. Ts'o, 2117 Folkstine Rd., Timonium, Md. 21093; William A. Carter, Orchard Park, N.Y.

[21] Appl. No.: 722,293

[22] Filed: Sep. 24, 1976

Related U.S. Application Data

[62] Division of Ser. No. 411,119, Oct. 30, 1973, Pat. No. 4,022,222.

[51] Int. Cl.$^2$ ................... A61K 45/04; C07H 21/02
[52] U.S. Cl. ................... 424/85; 424/180; 424/181; 536/28; 536/29
[58] Field of Search ................... 424/85, 180, 181

[56] References Cited

U.S. PATENT DOCUMENTS

| | | | |
|---|---|---|---|
| 3,843,629 | 10/1974 | Scheit et al. | 424/180 |
| 3,845,033 | 10/1974 | Harnden | 424/180 |
| 3,980,776 | 9/1976 | Ishida et al. | 424/85 |

Primary Examiner—Johnnie R. Brown
Attorney, Agent, or Firm—Walter G. Finch

[57] ABSTRACT

The present invention relates to the induction of interferon production in the cells of living organisms, including human beings. According to the invention, nucleic acid complexes, such as the polyriboinosinate and polycytidylate complex ($rI_n \cdot rC_n$), are modified to yield unpaired bases, (uracil or guanine) along the polycytidylate strand which render the complexes more readily hydrolyzable by nucleases present in living cells. The modified complexes retain their ability to stimulate interferon release by the cells but are rendered more vulnerable to destruction within the cells, the modified complexes being significantly less toxic than the original complexes. In addition, polyinosinate strand now has been prepared to contain 5-16% 2'-O-methyl inosinate residues, designated as ($rI_{5-20}$, 2'-MeI)$_n$. The new complex ($rI_{5-20}$, 2'-MeI)$_n \cdot rC_n$, exhibits 100-fold more activity than $rI_n \cdot rC_n$ as an interferon inducer in human cells.

11 Claims, 8 Drawing Figures

(a)     (b)     (c)

INDUCTION OF INTERFERON PRODUCTION BY MODIFIED NUCLEIC ACID COMPLEXES

The invention described herein was made in the course of work under a grant or award from the Department of Health, Education, and Welfare.

This is a divisional of patent application Ser. No. 411,119, filed Oct. 30, 1973, now U.S. Pat. No. 4,022,222.

BACKGROUND OF THE INVENTION

A. Field of the Invention

The invention generally relates to therapeutic compositions of matter, methods for producing said compositions, and methods for administering said composition to living organisms, including human beings. Particularly, the several embodiments of the invention allow protection of an organism against viral attack by stimulation of the cells of the organism to cause said cells to product an antiviral protein known as interferon.

B. Description of the Prior Art

Interferon is an antiviral protein released by animal cell in response to viral infection. It has long been known that RNA is a specific virion component which triggers the release of interferon in animal cell, both natural and synthetic double-stranded RNA's being known to stimulate interferon production. These double-stranded RNA molecules have not found utility as chemotherapeutic agents due to the toxicities thereof, such toxicity being related primarily to the presence of the double-helical RNA structure. It has been recently shown that the first step in interferon induction in the cells of a living organism, i.e., the absorption of the nucleic acid complex of polyinosinic acid annealed to polycytidylic acid ($rI_n \cdot rC_n$), is a rapid event, thereby suggesting that an intact primary structure of the inducer complex be present only for a brief period in the cell. The present invention now concludes that, once interferon induction is triggered, the continued presence of double-helical RNA is unnecessary and leads to secondary effects on the cell without increasing the magnitude of antiviral resistance. The invention thus involves provision of double-stranded nucleic acid complexes which, while retaining the capability of inducing interferon production in cells, are capable of being readily hydrolyzed by necleuses in the cells. Such nucleic acid complexes are duplications of the double-stranded virus genes which promote interferon production during viral attack, but which are modified to thereby be rendered less toxic to the cells due to the ability of said modified complexes to be more readily destroyed within the cells. The compounds of this invention have been disclosed previously from the laboratories (J.Molecular Biology 70:568[1972]).

In addition, now a new type of hypoxanthine-polynucleotides has been synthesized from a mixture of inosine 5'-diphosphates and 2'-O-methylinosine 5'diphosphates with $M.\ luteus$ polynucleotide phosphorylase. The procedure is similar to that previously disclosed from the laboratories (Biochemistry 11, 4931 [1972]). This type of hypoxanthine - polynucleotides contain 5–16% 2'-O-methylinosine residues together with 95–84% inosine residues correspondingly, designated as ($rI_{5\text{-}20}$, 2'-MeI)$_n$. These complexes, ($rI_{5\text{-}20}$, 2'-MeI)$_n \cdot rC_n$, are 100-fold more active than the $rI_n \cdot rC_n$ as interferon induces to human cells. Apparently this modification of the backbone of polyinosinate strand has a pronounced enhancement effect; therefore a less amount of ($rI_{5\text{-}20}$, 2'MeI)$_n \cdot rC_n$ is needed then $rI_n \cdot rC_n$ in protecting the human cells against viral diseases.

SUMMARY OF THE INVENTION

Interferon is normally produced by a living animal cell on viral attack, the double-stranded helical virus gene triggering the production of this antiviral protein by the cells.

The action of the double-stranded viral gene can be mimicked by the 1:1 complexes of polyriboinosinic and polyribocytidylic acids ($rI_n \cdot rC_n$). Two generally accepted conditions for such complexes to be adequate for induction of interferon production by cells are: (1) intactness of the double-stranded complex (with a $T_m$ higher than the incubation temperature); and, (2) adequate resistance to nucleases, i.e., to enzymatic activity in the cells. It has presently been found that additional structural and conformational requirements for the ($rI_n \cdot rC_n$) complex exist. Particularly, interruption of the $rC_n$ strand in the complex by unpaired bases such as uridine or guanine has less effect on the interferon induction capability of the resulting complex than does interruption of the $rI_n$ strand. Thus, for interferon induction, the structural requirements in strand continuity and base-pairing are more stringent in the $rI_n$ strand than in the $rC_n$ strand. Modifications to the $rC_n$ strand of the ($rI_n \cdot rC_n$) complexes are thus possible with retention of interferon induction capability and significant reduction of toxicity.

The present invention provides compositions of matter wherein duplications of these double-stranded helical virus genes are modified to an extent whereby the ability to induce interferon production in the cells is retained but the toxicities normally associated with such compounds and are reduced to an extent which allows their use as chemotherapeutic agents. In the first type of modification, double-stranded nucleic acid complexes which normally induce cellular interferon production are modified structurally so that the resulting molecule is readily hydrolyzed by nucleases within the cells. The modified nucleic acid complexes retain their ability to induce interferon production in the cells, but are rendered much less toxic than the unmodified double-stranded structures due to the ability of the cells to hydrolyze the modified complexes shortly after interferon production has been induced.

In the second type of modification, the ribosyl backbone of polyinosinic acid in the $rI_n \cdot rC_n$ complex is partially replaced (to the extent of 5–16%) by the 2'-O-methylribosyl residues. The modified complexes ($rI_{5\text{-}20}$, 2'MeI)$_n \cdot rC_n$ were found to be 100 fold more active than $rI_n \cdot rC_n$ as inducer for interferon in the human cells.

Toxicity reduction in the first type of modified ($rI_n \cdot rC_n$) complexes is accomplished by structural modification of said complexes, a general modification being the introduction of a nucleotide into the $rC_n$ strand to prevent normal pairing between the strands, thereby to produce a "weak point" or chemical position on the strand which is vulnerable to attack by nucleases in the cells. While the modified complex retains sufficient structural integrity to induce interferon production in cells, this vulnerability to enzymatic activity allows relatively rapid hydrolysis thereof within the cells. Thus, the modified complex structure is destroyed after its function as an interferon inducer is served, destruction of the complex preventing harmful effects which would be caused thereby were said complex allowed to remain in the cell. Since the continued presence of this double-stranded, helical complex does not increase antiviral resistance in the cell once induction has been triggered, nothing is lost by destruction of the complex, the reduction in toxicity to the cell and to the organism allowing its use as a therapeutic agent for protection of an organism against viral attack.

In the second type of modified ($rI_n \cdot rC_n$) complexes, the $rI_n$ strand is replaced by a ($rI_{5-20}$, $2'MeI)_n$ strand. This new complex, ($rI_{5-20}$, $2'MeI)_n \cdot rC_n$, is 100 fold more active than $rI_n \cdot rC_n$; therefore, a much lower dosage of this modified complex is needed for the same protection against viral attack to the human cells.

It is therefore an object of the invention to provide compositions of matter and a method for protecting against viral infection in a cell by stimulating the production of interferon by the cell.

It is another object of the invention to provide a method for structuring, on a molecular scale, double-stranded, helical nucleic acid complexes to render said complexes capable of inducing interferon production in an organism while being non-toxic to the organism in therapeutic dosages.

It is a further object of the invention to provide therapeutic agents comprised of ($rI_n \cdot rC_n$) complexes which are rapidly hydrolyable by enzymatic activity in living cells after induction of interferon production therein.

It is an additional object of the invention to provide therapeutic agents comprised of ($rI_{5-20}$, $2'MeI)_n \cdot rC_n$ which may be many-fold more active than $rI_n \cdot rC_n$ as human interferon inducer.

Further objects and advantages of the invention will become more readily apparent from the following detailed description of the preferred embodiment of the invention.

DESCRIPTION OF THE PREFERRED EMBODIMENTS

Figure 1:
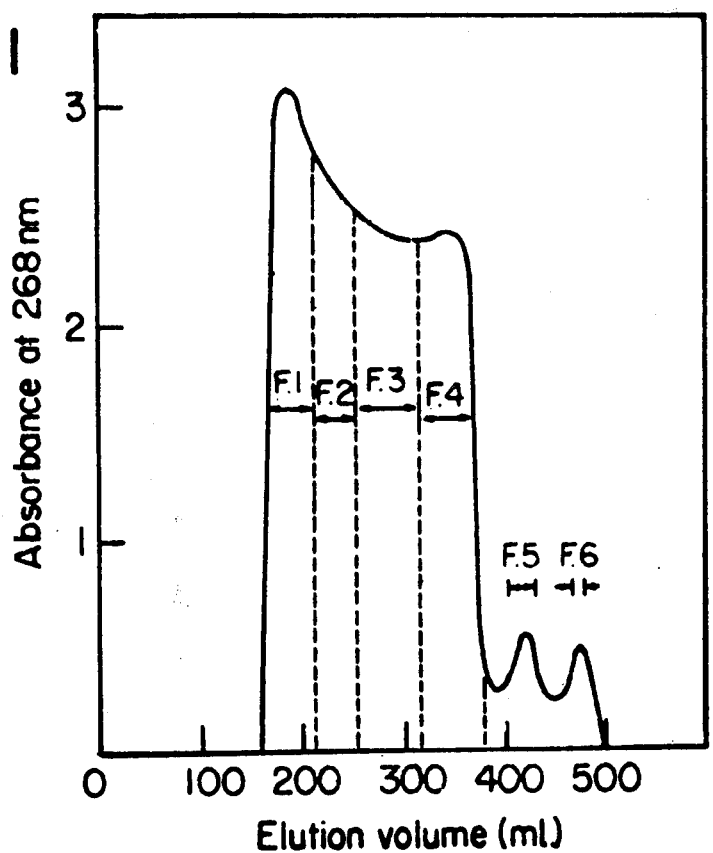
FIG. 1 is a graphic illustration of an elution pattern from a Sephades G50 column (2.5cm × 95 cm) of a hydrolysate of $r(C_{20},G)_n$ by RNase $T_1$, the designations Fr. 1–6 indicating "fractions 1 through 6"

The present compositions of matter and methods relative to their use generally depend in the several embodiments thereof on the chemical modification of an interferon inducing nucleic acid complex to render said complex less toxic to a living animal cell. The chemically modified complexes disclosed herein retain the capability of the unmodified complexes for inducing the production of interferon by cells while being rendered more readily hydrolyzable by nucleases in the cells relative to the unmodified complexes. The increased hydrolysis capability of the modified complexes renders said complexes less toxic to the cells due to the relatively rapid destruction of the complexes after interferon induction.

The double-stranded, helical nucleic acid complexes which are of concern in the present invention may be modified by mismatching of bases, thereby causing a "looping-out" from the helix at the point or points thereon where the bases are caused to be unpaired; by strand-interruption formation of oligomer-polymer complexes; and by disposition of hydrocarbon groups, such as a methyl group, within the helical structure. In the first of these particular modifications, pairing of bases in the two strands of the complex is interrupted to produce a "weak" point or vulnerable chemical position in the complex which is subject to attack by nucleases in the cells. Unpaired bases such as uridine or guanine interrupt either of the strands of a nucleic acid complex, such as the rC strand of the complexes of polyriboinosinic and polyribocyticylic acids (poly rT·rC or $rI_n \cdot rC_n$, which is polyinosinic acid annealed to polycytidylic acid), without interferring with interferon induction capability (thereby preserving antiviral function). However, this interruption permits accelerated hydrolysis of the complex, thus reduction in toxicity thereof, because of the formation of a weakened position in the structure of the complex which is more subject to chemical attack and hereby hydrolysis by nucleases in the cells. Similarly, bond breakage in the double-stranded helical structure effected by strand-interruption formation of oligomer-polymer complexes or by disposition of hydrocarbon groups in the structure provides sites in the molecular structure of the complex which are more readily susceptible to hydrolyzing enzymatic attack.

The nucleic acid complex, $rI_n \cdot rC_n$, noted above proves particularly valuable as a basic structure for modification into low toxicity interferon inducers. Data to be presented hereinafter show that, for interferon induction, the structural requirements in strand continuity and base-pairing are more stringent in the $rI_n$ strand than in the $rC_n$ strand. Thus, modified $rI_n \cdot rC_n$ complexes wherein the $rC_n$ strand is interrupted prove most useful. Since it has been found that the triggering of human cells for interferon production through the absorption of $rI_n \cdot rC_n$ is completed within a few minutes, the intact primary structure of the inducer complex is required to be present in the cell only briefly. Once the induction has been triggered, the continued presence of the double-stranded, helical $rI_n \cdot rC_n$ is not necessary and leads to harmful effects without increasing antiviral resistance. According to this kinetic factor, modification of the $rI_n \cdot rC_n$ complex to a more readily hydrolyzable form as previously described does not reduce antiviral resistance. Two modified complexes of $rI_n \cdot rC_n$ which have been found to retain the interferon induction capability of the unmodified complex but which are relatively rapidly hydrolyzed by nucleases within the cells are $rI_n \cdot r(C_{12-13}, U)_n$ and $rI_n \cdot r(C_{20-29}, G)_n$ where U represents uridine and G represents guanine. Other complexes so structured include $rI_n \cdot r(c_{22}, U)_n$ and $rI_n \cdot r(C_7, U)_n$. The formation of and characteristics of these modified complexes will be described hereinafter.

Exposure of an organism to massive dosages of either the unmodified $rI_n \cdot rC_n$ or the modified complexes results in toxic effects due to the inability of the organism to effectively dispose of said substances within a sufficiently short period of time. However, those dosages normally associated with therapeutic practice are rendered harmless with the modified complexes through enzymatic hydrolysis in the cells much more readily than in the unmodified $rI_n \cdot rC_n$. Modification of the backbone of the nucleic acid complexes can even produce greater induction capability as is evidenced by the $(rI_{6-19}, mI)_n \cdot C_n$ complex which exhibits 100-fold more activity than $rI_n \cdot rC_n$ as an interferon inducer in human cells. Effective dosages of these modified complexes vary depending on the interferon induction capability and hydrolysis rates thereof, a range of from 1 to 100 μgm/kilogram of body weight being safely and effectively administered, for example, to mice. Such concentration of the unmodified $rI_n \cdot rC_n$ complex are highly toxic.

Interruption of the acid strands in these nucleic acid complexes produce imperfect, or modified, complexes having $T_m$ values substantially higher than 37° C, the modified complexes being protectable from nucleases by complex formation with polylysine without impairment of the induction ability thereof. Addition of poly L-(or D-) lysine to $rI_n$-oligocytidylate complexes, e.g., $rI_n \cdot (Cp)_{23}G > p$, or to the modified complexes specifically pointed out hereinabove rendered said complexes resistant to enzymatic destruction without affecting antiviral activity.

The following methods, procedures, and materials have been used to conduct portions of the work resulting in the present invention, a discussion of which is provided for a better understanding of the practice of the invention.

Source, Composition, and Preparation of Substances Used

Enzymes and nucleoside diphosphates: Polynucleotide phosphorylase (Micrococcus luteus, lyophilized powder) was purchased from PL Biochemicals, Inc., Milwaukee, Wisconsin. Bovine pnacreases RNase, RNase $T_1$ and Escherichia coli alkaline phosphatase were obtained from Worthington Biochemical Co., Freehold, New Jersey, IDP (trisodium salt) and UDP (trisodium salt) were obtained from Miles Laboratories, Elkhart, Indiana. CDP (trisodium salt), CDP (trilithium salt) and GDP (disodium salt) were purchased from PL Biochemicals, Inc., Schwarz BioResearch, Inc., Orangeburg, New York, and from Calbiochem, Los Angeles, California, respectively.

The preparation of 2'-O-Methylinosine 5'-diphosphates or related 2'-O-alkyl nucleotides have been recently disclosed in a paper cited in Biochemistry, (1972) 11, 4931 entitled "A Novel Procedure For the Synthesis of 2'-O-Alkyl Nucleotides", by I Tazawa et al.

Polynucleotides $rI_n$ and $rC_n$ were purchased from Miles Laboratories, Elkhart, Indiana. The maximum molar extinction coefficients of 10,000 (in 0.005M sodium acetate, pH 6.0) and 6300 (in 0.01 M-sodium phosphate, pH 7.5) were used for $rI_n$ and $rC_n$, respectively. $r(I_{39}, U)_n$, $r(I_{21}, U)_n$, $r(C_{22}, U)_n$, $r(C_4, U)_n$ and $r(C_{20}, G)_n$ were prepared in the laboratory by enzymic polymerization of nucleoside diphosphates using polynucleotide phosphorylase. The reaction mixture contained nucleoside dephosphates (40 mM), 0.15 M-Tris.HCl(pH 8.2), 10 mM-MgCl$_2$, 0.4 mM-EDTA and M.luteus polynucleotide phosphorylase (2 mg/ml. of the reaction mixture). After incubation at 37° for 5 to 7 hr, 0.1 vol. of 5% sodium dodecyl sulfate and 0.1 vol. of 10% phenol were added to the reaction mixture, which was shaken for 5 min. Crystalline phenol (approximately 1 g/5ml. of the mixture) was added to the mixture, which was shaken vigorously. The aqueous layer was separated by contrifugation, transferred to another container, and was treated with phenol once more. The final aqueous layer was collected and dialyzed successively against 50 mM-NaCl/5 mM-EDTA, 5 mM-CaCl/0.5 mM-EDTA and distilled water. After dialysis, the polymer solution was free from the nucleoside diphosphates, as determined by paper chromatography. The polynucleotides in aqueous solution were stored at −17° C. Base compositions of the co-polymers were determined by hydrolysis of the polymer to its constituent nucleotides, followed by conversion to the corresponding nucleosides by E. coli alkaline phosphatase. The nucleosides were separated by paper chromatography and quantitated by u.v. absorption. The polymers were hydrolyzed by 0.3 M-KOH except for $r(C_{20}, G)_n$ which was hydrolyzed by a mixture of pancreatic RNase and RNase $T_1$. The following solvent systems were used for paper chromatography; isopropanol/water, 7:3 for copoly(I,U)'s; n-butanol/formaldehyde/water, 77 : 10 : 13 for co-poly (C,U)'s; isopropanol/ammonia/water, 7 : 1 : 2 for $r(C_{20}, G)_n$. The molar extinction coefficients of $r(I_{39}, U)_n$ and $r(I_{21}, U)_n$ were assumed to be the same as that of $rI_n$. Likewise, the $rC_n$ value was used for $r(C_{22}, U)_n$, $r(C_{13}, U)_n$ and $r(C_{20}, G)_n$. Extinction coefficients of $r(C_7, U)_n$ and $r(C_4, U)_n$ have been determined to be 6700 and 6800 (in 0.01 MTris.HCl, pH 7.5), respectively, by phosphorus analysis. Table 1 summarizes the preparation, base composition and sedimentation coefficient of the copolymers prepared.

Table I

| Polymer | Substrates (μmoles) in enzymic reaction | Yield (%) | Base composition of co-polymers | Sedimentation coefficient($S_{30.hr}^+$) |
|---|---|---|---|---|
| Preparation, base composition and sedimentation coefficient of the synthetic copolymers | | | | |
| poly ($I_{39}$,U) | IDP (600) + UDP (30) | 42 | 1 : U = 39.4 : 1 | 10.2 |

Table I-continued

Preparation, base composition and sedimentation coefficient of the synthetic copolymers

| Polymer | Substrates (μmoles) in enzymic reaction | Yield (%) | Base composition of co-polymers | Sedimentation coefficient($S_{30.hr}$)[+] |
|---|---|---|---|---|
| poly ($I_{21}$,U) | IDP (600) + UDP (60) | 40 | I : U = 20.8 : 1 | 7.9 |
| poly ($C_{22}$, U) | CDP (578) + UDP (30) | 38 | C : U = 21.8 : 1 | 3.8 |
| poly ($C_{13}$,U) | CDP (578) + UDP (60) | 44 | C : U = 12.7:1 | 6.7 |
| poly ($C_1$,U) | CDP (600) + UDP (120) | 40 | C : U = 7.0:1 | 3.8 |
| poly ($C_4$,U) | CDP (500) + UDP (200) | 38 | C : U = 4.1 : 1 | 6.8 |
| poly ($C_{20}$,G) | CDP (1000) + GDP (50) | 47 | C : G = 20.4 : 1 | 3.4 |

[+]Measurements were carried out in minimal Engle's salt solution. The sedimentation coefficients of poly (I) and poly(C) used in this study were 7.3 s and 3.8 s, respectively.

The preparation of the poly 2'-O-methylinosinic is also similar to that disclosed in Biochemistry (1972) 11, 4931, entitled "A Novel Procedure For The Synthesis of 2'-O-alkyl nucliotides", by I Tazawa. However, in this procedure, an attempt has been made to make a hybrid containing both residues, i.e., the residues of inosimic as well as 2'-O-methylinosinic, both residues being synthesised together in the same strand in the new type of polynucleotides. In this case, a certain proportion of both substrates are put into the mixture, i.e., certain proportions of inosinic 5'-diphosphate and certain proportions of 2'-O-methylinosinic 5'-diphosphate were put into the enzyme reaction mixture. Incubation followed quite closely as that reported in Biochemistry (1972) 11, 4931, entitled "A Novel Procedure For The Synthesis of 2'-O-alkyl nucliotides", by I. Tazawa, for the production of poly 2'-O-methylinosinic and as quoted in this embodiment for the synthesis of poly 2'-O-inosinic.

Oligoinosinates

Oligoinosinates were prepared by controlled alkaline hydrolysis of $rI_n$, followed by treatment with HCl and alkaline phosphatase. They were isolated by DEAE-cellulose column chromatography and were characterized. The following extinction coefficients were used for the oligomers: 11,400 for $(Ip)_2I$, 10,800 for $(Ip)_5I$, 10,400 for $(Ip)_9I$, and 10,200 for $(Ip)_{16}I$.

Degradation of $r(C_{20},G)_n$ with RNase $T_1$

About 600 optical density units (at 268 nm) of $r(C_{20},G)_n$ were incubated with 350 units of RNase $T_1$ at 37° C for 3 hr in 12.5 ml. of 0.05 M-Tris.HCl (pH 7.5)/1mM-EDTA. After incubation, the reaction mixture was lyophilized, dissolved in 1 ml. of water and applied to a column of Sephadex[R] G50 (2.5 cm × 90 cm). The column was eluted with water, the elution profile being shown in FIG. 1. Six fractions were arbitrarily selected, as shown in the Figure. Fractions 5 and 6 had similar u.v. spectra to cytidine and guanosine, respectively and were not characterized further. Fractions 1 to 4 all showed u.v. spectra similar to that of poly C($\lambda_{max}$268 nm in 0.01 M-Tris.HCl, pH 7.5). The general formula of $(Cp)_n$ G>p was assigned to these four fractions, considering the specificity and the amount of RNase, $T_1$ used. Incubation of these fractions with a mixture of pancreatic RNase, RNase $T_1$ and E. coli alkaline phosphatase gave cytidine and guanosine exclusively. The average chain-length of these fractions was determined from the cytidine : guanosine ratio, and is shown in Table 2. The following extinction coefficients were arbitrarily chosen for fractions 1 to 4, considering ε's of oligocytidylates and the presence of one guanylate residue per molecule: fraction 1, 6600; fraction 2, 6800; fraction 3, 7000; fraction 4, 7300, in 0.1 M-Tris.HCl, pH 7.5, at room temperature.

Table 2

Average chain length and base composition of the various fractions of $(C_p)_n\tilde{G}$>p obtained by RNase $T_1$ hydrolysis of poly $(C_{20}G)$[+]

| Fraction | Cytidine (μmoles) | Guanosine (μmoles) | C : G ratio | Average chain length |
|---|---|---|---|---|
| 1 | 2212 | 47.2 | 46.9 : 1 | |
|   | 1753 | 35.6 | 49.2 : 1 | 49.1 |
| 2 | 1405 | 38.4 | 36.4 : 1 | |
|   | 1559 | 46.5 | 33.5 : 1 | 36.1 |
| 3 | 1399 | 62.1 | 22.5 : 1 | |
|   | 1312 | 65.7 | 23.6 : 1 | 21.1 |
| 4 | 1001 | 86.5 | 11.6 : 1 | |
|   | 979 | 86.6 | 11.3 : 1 | 12.4 |

[+]Experiments were carried out in duplicate.

Formation of poly-and/or ologonculeotide complexes $rI_n$ was mixed with $rC_n$, co-poly(C,U)'s, $r(C_{20},G)_n$ and $(Cp)_nG$>p at room temperature in buffer A to form the complexes; likewise, $rC_n$ was mixed with co-poly(I,U)'s and oligo(I)'s. Since $(Ip)_2I$ and $(Ip)_5I$ do not form complexes with $rC_n$ at room temperature, their mixtures with $rC_n$ were kept at about 4° C before experiments. All mixtures were kept at least 3 hr at appropriate temperatures to ensure complete complex formation before experiments. Stoichiometry of the mixing was always 1 : 1, with respect to inosine and cytidine residues and concentrations of the complexes were expressed in terms of the I-C residues.

Formation of the complexes between polylysines and the poly-and/or oligonucleotide complexes Preformed polynucleotide complexes in buffer A were added dropwise to an equal volume of the polylysine solutions in the same media, with stirring. Polynucleotide and polylysine concentrations were adjusted to give the desired value upon mixing equal volumes of the solutions. At the concentration level of 1 to 5 × $10^{-5}$ M-residue of polynucleotide, formation of 1 : 1 complex with poly-L-lysine or poly-D-lysine at room temperature does not lead to a significant amount of precipitation. This was indicated by the absence of turbidity (elevation of absorbance at 320 nm) and little loss (less than 10%) of material after centrifugation at 3000 g for 15 min. However, such a solution always turns cloudy and begins to absorb strongly at 320nm, during the melting process, at elevated temperature, and upon cooling. It was concluded that the complex between single-stranded polynucleotide and polylysine is even less soluble than the complex of polylysine/$r(I)_n\cdot r(C)_n$.

For the preparation of $r(Ip)_{12}I\cdot rC_n\cdot$poly-l-lysine ternary complex, $r(Ip)_{12}I\cdot rC_n$ was made in 2 m-NaCl/0.01 M-NaPO$_4$/0.001 M-MgCl$_2$ and was kept at about 5° C for 1 hr. This solution was added to the cooled poly-L-lysine solution in the same solvent. This solution was dialyzed at 4° C successibely against 0.01 M-NaPO$_4$/0.001 M-MgCl$_2$ containing 1 M-NaCl (for 4 hr), 0.5 M-MaCl (for 4 hr), 0.25 M-NaCl (for 10 hr) and finally 0.15 M-NaCl (for 6 hr).

Table 3

The effect on non-base-paired regions in $rI_n$ or $rC_n$ on interference induced by $rI_n \cdot rC_n$ complex

| Complex[+] | Concn. (of mononucleotides) (M) | ,U) protection, % Exp. A[++] | Exp. B[++] | Virus yield Exp. A[++] | Exp. B[++] | Exp. C[++] | Interferon (units/ml.) Exp. A[++] | Exp. B[++] |
|---|---|---|---|---|---|---|---|---|
| $r(I_{21},U)_n \cdot rC_n$ | $1 \times 10^{-5}$ | 10 | 7 | — | $3.3 \times 10^9$ | — | — | — |
| $r(I_{21},U)_n \cdot rC_n$ | $1 \times 10^{-4}$ | 20 | 8 | $3.3 \times 10^8$ | $3.3 \times 10^9$ | — | 0 | — |
| $r(I_{21},U)_n \cdot rC_n$ | $1 \times 10^{-3}$ | 100 | 50 | $1.6 \times 10^6$ | $7.2 \times 10^7$ | — | 0 | — |
| $r(I_{39},U)_n \cdot rC_n$ | $1 \times 10^{-5}$ | 12 | 7 | $6.9 \times 10^6$ | — | — | — | — |
| $r(I_{39},U)_n \cdot rC_n$ | $1 \times 10^{-4}$ | ,U)$_{45}$ | $3.0 \times 10^7$ | $7.0 \times 10^9$ | — | 0 | — | — |
| $r(I_{39},U)_n \cdot rC_n$ | $1 \times 10^{-3}$ | 99 | 100 | $1.8 \times 10^4$ | $1.0 \times 10^7$ | — | 0 | — |
| $rI_n \cdot r(C,U)_n$ | $1 \times 10^{-3}$ | 10 | — | $8.0 \times 10^8$ | — | — | — | — |
| $rI_n \cdot r(C_4,U)_n$ | $1 \times 10^{-5}$ | 30 | 35 | — | — | $1.2 \times 10^8$ | — | — |
| $rI_n \cdot r(C_4,U)_n$ | $1 \times 10^{-4}$ | — | 30 | — | — | $2.1 \times 10^6$ | — | — |
| $rI_n \cdot r(C_4,U)_n$ | $1 \times 10^{-3}$ | — | 19 | — | — | $1.0 \times 10^6$ | — | — |
| $rI_n \cdot r(C_7,U)_n$ | $1 \times 10^{-5}$ | 50 | 21 | — | $5.7 \times 10^8$ | — | — | — |
| $rI_n \cdot r(C_4,U)_n$ | $1 \times 10^{-4}$ | — | 87 | — | $1.0 \times 10^7$ | — | — | — |
| $rI_n \cdot r(C_7,U)_n$ | $1 \times 10^{-5}$ | 100 | 33 | $9.0 \times 10^3$ | $1.3 \times 10^3$ | — | — | <5 |
| $rI_n \cdot r(C_{13},U)_n$ | $1 \times 10^{-4}$ | 100 | — | $6.0 \times 10^3$ | — | — | 18 | — |
| $rI_n \cdot r(C_{13},U)_n$ | $1 \times 10^{-3}$ | 100 | — | — | — | — | 10 | — |
| $rI_n \cdot r(C_{22},U)_6$ | $1 \times 10^{-3}$ | 100 | — | $3.3 \times 10^4$ | — | — | — | — |
| $rI_n \cdot r(C_{22},U)_n$ | $1 \times 10^{-4}$ | 100 | — | $3.0 \times 10^3$ | — | — | 20 | — |
| $rI_n \cdot r(C_{22},U)_n$ | $1 \times 10^{-3}$ | 100 | — | — | — | — | 10 | — |
| $rI_n \cdot rC_n$ | $1 \times 10^{-5}$ | 98 | 92 | — | $1.1 \times 10^6$ | $2.4 \times 10^7$ | — | <5 |
| $rI_n \cdot rC_n$ | $1 \times 10^{-4}$ | 98 | — | $3.8 \times 10^3$ | — | — | 26 | — |
| $rI_n \cdot rC_n$ | $1 \times 10^{-3}$ | 100 | — | $3.0 \times 10^2$ | — | — | 40 | — |
| None | | 11 | — | $9.0 \times 10^5$ | $3.3 \times 10^9$ | $6.6 \times 10^5$ | None | — |

[+]All exposures were for 60 min at 37° C at concentrations indicated. Cells were washed (twice in minimal Eagle's medium) and minimal Eagle's medium (containing 12% fetal calf serum) was added. Measurements of interference and interferon are described in the text.
[++]Experiments A, B and C were conducted at different times with different batches of cells, which had different sensitivities towards interferon induction and virus yield. Therefore, internal controls are provided for each group of experiments.

Hydrolysis of nucleic acid complexes and the ternary complexes with polylysines by pancreas RNase $rI_n \cdot rC_n r(I_{21},U)_n \cdot rC_n$, $rI_n \cdot r(C_4, U)_n$, $rI_n \cdot (Cp)_{48}G > p$ and their complexes with L- and d.polylysine were prepared as mentioned above. The nucleotide concentration used was $1 \times 10^{-5}$ M, and the ratio of phosphate (nucleotide) to nitrogen (lysine) was 1 : 1. The low nucleotide concentration was employed to avoid precipitation of the complex by polylysine. Bovino pancreas RNase was dissolved in distilled water to a concentration of 1 mg/ml.; a μd. of the enzyme solution was then added to 36 ml. of the complex solution and mixed well. The mixture was kept at room temperature; its absorption spectra was recorded at appropriate time intervals using a cell with a 10-cm path-length.

Experiments have been done to ensure that the lack of increase of absorbance of the polynucleotide complexes with polylysine in the presence of the nuclease is a reliable indicator that the polynucleotides remain intact. This was done by addition of saturated $(NH_4)_2SO_4$ solution to a final concentration of 20% saturation. Under this condition, the nuclease activity is prohibited and the polylysino-polynucleotide complex dissociates. No increase in absorbance of the polylysino-polynucleotide complex (1 : 1) after incubation with the enzyme due to the addition of $(NH_4)_2SO_4$ was found (after adjustment for dilution). Addition of $(NH_4)_2SO_4$ did not change the increase of absorbance caused by polynucleotide degradation after incubation with enzyme in the absence of polylysine.

Physico-chemical properties

Absorption spectra were measured in a well-known fashion.

The $T_m$ was defined as the temperature at which half of the total optical change occurred. Sedimentation coefficients were determined on a Spinco model E analytical ultracentrifuge equipped with a photoelectric scanner. The concentration of those samples was adjusted to give 0.5 to 0.8 optical density unit at 265 nm.

Biological studies

Solutions

Buffer A is 0.15 M-NaCl, 0.01 m-sodium phosphate (pH 7.2), 0.001 M-MgCl$_2$. This buffer was used for both physical and biological studies so that the results could be compared directly. Minimal Eagle medium was prepared to contain either 12% or 6% fetal calf serum as specified, and glutamino (2 mM), penicillin G (200 units/ml.) and streptomycin (200 μg/ml.) were added just before use. Saline D is 0.14 M-NaCl, 0.0017 M-Na$_2$HPO$_4$, 0.0054 M-KCl, 0.0023 m-KH$_2$PO$_4$ and 0.6 mg of phenol red poor ml. Trypsin (0.2%) was prepared in saline D to contain 0.005 M-ethylenediaminetetraacetic acid. National Cancer Institute medium 2X was used as the plaque-overlay medium.

Cells

Human neonatal fibroblasts, grown as monolayers, were maintained in 75 cm$^2$ plastic flasks; for interferon studies, they were transferred to plastic panels (35 mm × 10 mm). These cells, which produce relatively small amounts of extracellular interferon in vitro were harvested and passed in the standard manner.

Preparation of virus stocks

Bovine vesicular stomatitis virus, New Jersey serotype, was harvested from infected mouse embryo and mouse amnion cells to yield a titer of 1 to 10 × 10$^8$ plaque-forming units/ml.; the virus stock, usually diluted 100-fold, was stored at −70° C.

Interferon induction and assay

To obtain a sensitive measure of interference, several measurements of the antiviral state were quantitated simultaneously; (a) interferon assays and two indices of intracellular interference; (b) colorimetric assay of viral cytopathicity and (c) reduction in viral yield. The latter method enables us to compare the antiviral protection in the regions near 0% and 100% of cell survival, where the former method fails. Usually the cells were used between passages 7 and 25, because the sensitivity of these cells to $rI_n \cdot rC_n$ changes from time to time, each set of experiments contains an internal reference, usually $rI_n \cdot rC_n$ studied at $10^{-3}$ to $10^{-5}$ M.

Cells were exposed to polynucleotide complexes in minimal Eagle medium at concentrations specified for 1 hr and then washed three times before reincubation in fresh medium at 37° C. (a) Interferon was harvested from the extracellular fluids 18 hr later and measured colorimetrically using bovine vesicular stomatitis virus as the challenge virus. Assays were carried out in duplicate or triplicate and reference interferons (supplied by the Biologic Resources Branch, National Institutes of Health) were also processed from time to time to confirm the sensitivity of the assay system. Assays of intracellular interference: (b) Intracellular resistance as determined colorimetrically. Generally a multiplicity of infection of approximately 1 plaque-forming unit/cell was used. Resistance (%) was defined as the ratio of number of viable cells (after virus infection), to the number of living cells (only mock infected). The colorimetric titration (in duplicate) was usually made 72 hr after infection. (c) Reduction in virus yield as a measurement of intracellular interference. Cells were treated with bovino vesicular stomatitis virus ($10^7$ plaque-forming units per dish, multiplicity of infection approximately 20) for 60 min and the unabsorbed virus than removed; the cells were washed twice and the cultures incubated for 20 hr in fresh medium. Virus titer was then determined (in duplicate) in mouse cells by plaque titrations.

Criteria for identification of human interferon

The interferons were shown initially to fulfill these criteria: they were trypsin-sensitive, non-dialysable, and did not sediment at 105,000 g for 2 hr. They demonstrated species specificity, as shown by the absence of activity in mouse or chick cells. Representative interferons obtained in these studies were chromatographed on Sephadex$^R$ G150 and G200, yielding a single peak of activity corresponding to a molecular weight of approximately 96,000 daltons.

Interpretation of Results

The general approach

It has been generally recognized that in order for the ribosyl polynucleotides to be effective interferon inducers, they must possess the secondary structure of a double-stranded helix. In addition, polynucleotides need to be resistant to nucleases in order to remain as macromolecules for a sufficient length of time; polynucleotides are usually much less sensitive to attack when they are in a helical complex. Therefore, these two basic requirements have to be recognized for any modification of the $rI_n \cdot rC_n$ complex. For instance, the modified $rI_n \cdot rC_n$ complex (in Eagle's balanced salt solution, buffer A) should have a $T_m$ substantially above the incubation temperature (37° C) of the cells. The sensitivities of these modified complexes to nucleases have been assayed; when these compounds have been found to be more susceptible than the parent $rI_n rC_n$ complex, measures were taken to increase their resistance. The remedial measure adopted for such a purpose is the introduction of polylysine (both the D-form and the L-form) for the formation of polycation-polynucleotide complexes, which have been shown to be very resistant to nucleases. This leads to an investigation of the biological activity of the polylysine-polynucleotide complex. It is important to show that the addition of the polylysine to $rI_n \cdot rC_n$ does not significantly alter the interferoninducing capability of the original polynucleotide complex. With the above strategy in mind, we have examined the modified $rI_n \cdot rC_n$ complex with respect to its thermal melting properties, its biological activity as an interferon inducer in human cells, its sensitivities to nucleases and the effect of complex formation with polylsine on all these aspects.

$rI_n \cdot rC_n$ Complexes containing unpaired bases

Figure 2:
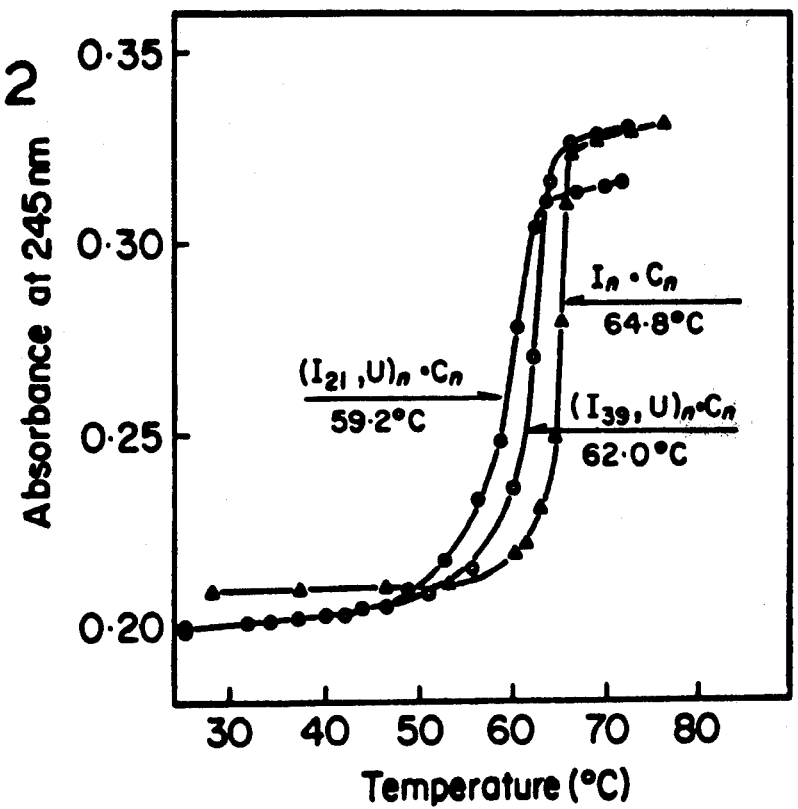
FIG. 2 is a graphic illustration of melting curves of $rI_n \cdot rC_n$, $r(I_{39},U)_n \cdot rC_n$, and $r(I_{21},U)_n \cdot rC_n$ in minimal Eagle's salt solution, nucleotide concentration being $4 \times 10^{-5}M$ in I + C.
Figure 3:
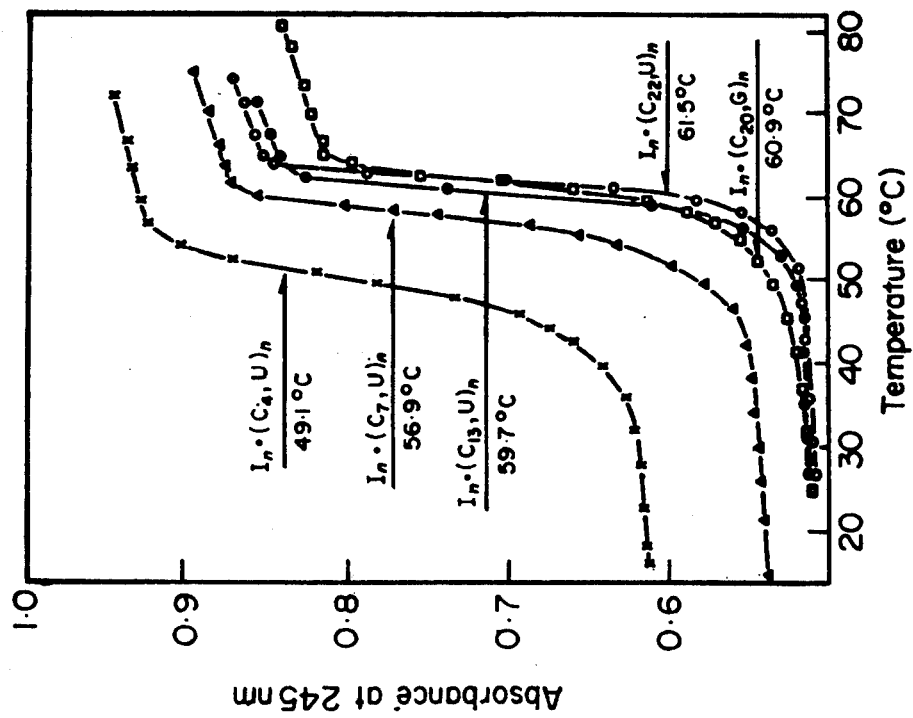
FIG. 3 is a graphic illustration of melting curves of $rI_n \cdot r(C_{22}, U)_n$, $rI_n \cdot r(C_{13},U)_n$, $rI_n \cdot r(C_7, U)_n$, $rI_n \cdot r(C_4,U)_n$, and $rI_n \cdot r(C_{20}, G)_n$ in minimal Eagle's salt solution, nucleotide concentration being $1 \times 10^{-4}M$ in I + C.

Uridylate residues were introduced into the $rI_n$ strand and the $rC_n$ strand as the unpaired bases and in one special case guanylate was introduced to the $rC_n$ strand for the same purpose. The composition of these presumably random co-polymers and their sedimentation coefficients are shown in Table 1. These polynucleotides have a molecular weight ranging from 30,000 to 100,000 as judged from their sedimentation coefficient values. The melting profiles and the $T_m$ values of seven imperfect I·C complexes in buffer A (Eagle's salt solution), along with the parent $rI_n \cdot rC_n$, are shown in FIGS. 2 and 3. All of the complexes gave highly co-operative profiles with the $T_m$ (50° to 60° C) slightly lower than that of $rI_n \cdot rC_n$ (64.8° C), but substantially above 37° C, the incubation temperature. The small reduction in $T_m$ and slight broadening of the helical-coil transition profile are to be expected from these imperfect complexes.

When these imperfect complexes were evaluated for antiviral functions (Table 3), it was immediately apparent that the introduction of U into the $rI_n$ strand caused a much greater reduction in activity of the resultant complex than when introduced into the $rC_n$ strand. The biological activities of $rI_n \cdot r(C_{13}, U)_n$ and $rI_n \cdot r(C_7, u)_n$ are significantly higher than those of $r(I_{39}, U)_n \cdot rC_n$ and $r(I_{21}, U)_n \cdot rC_n$ in two separate experiments (Table 3), even though all of these complexes are helical at 37° C. The $T_m$ of $r(I_{39}, U)_n \cdot rC_n$ was only 2° C lower than that of the $rI_n \cdot rC_n$ (FIG. 2), but the biological activity is reduced by about 100-fold. On the other hand, while the $rI_n \cdot r(C_{13}, U)_n$ has a $T_m$ of about 5° C lower than that of $rI_n \cdot rC_n$, the biological activity of this imperfect complex is only slightly reduced. Even the $rI_n \cdot r(C_7, U)_n$ is definitely active, although the activity of $rI_n \cdot r(C_4, U)_n$ is just marginal and is not responsive to an increase in concentration. Previously, it was noted that formation of an $r(C, U)_n$ copolymer with a 1:1 ratio results in a biologically inert $rI_n \cdot r(C, U)_n$ complex. Within experimental error, $rI_n \cdot r(C_{22}, U)_n$ is just as active as $rI_n \cdot r(C)_n$.

OLigo I·$rC_n$ and $rI_n$·oligo C complexes, the effect of strand interruption

Figure 4:
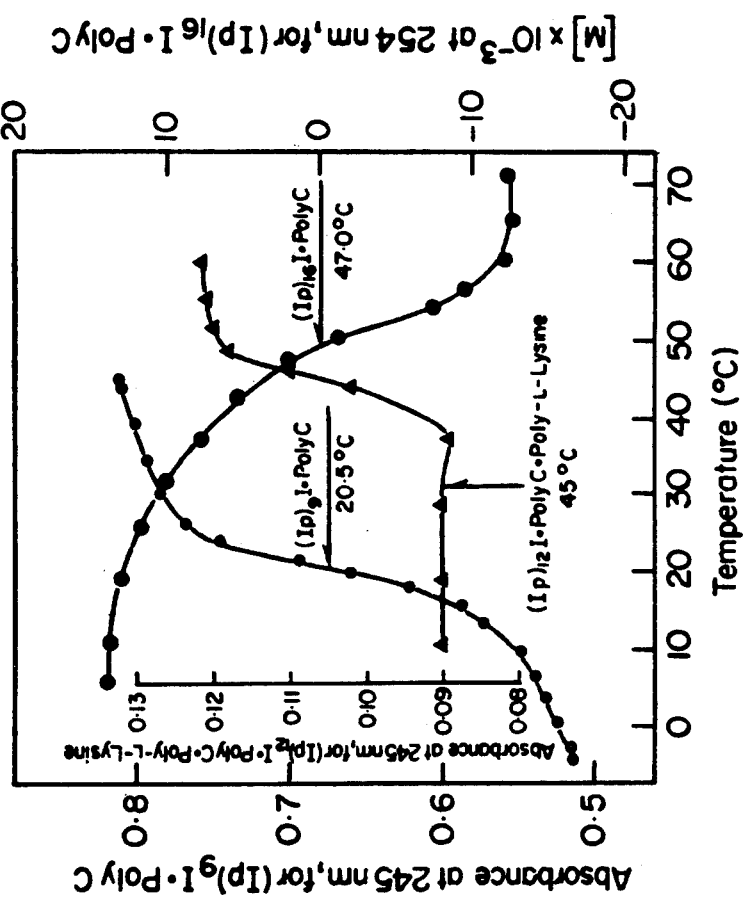
FIG. 4 in a graphic illustration of melting curves of $(Ip)_9 I \cdot rC_n$ (Nucleotide concentration $1 \times 10^{-4}M$) and $(Ip)_{12} I \cdot rC_n \cdot$poly-L-lysine (initial nucleotide concentration $2 \times 10^{-5}M$, P/N ratio = 1) in minimal Eagle's salt solution, and $(Ip)_{16} I \cdot rC_n$ (nucleotide concentration $1 \times 10^{-3}M$) in 0.15m NaCl, 0.01M $MgCl_2$, and 0.001M sodium phosphate (pH7.4)

It has been shown that the biological activities of poly (C)·hexainosinate complex were only negligible without the enhancing effect of DEAE-dextran. (I)·poly In the present studies, we examined this system in more detail and tried to establish the requirement of chain-length of either oligo (I) or oligo (C), which, when complexed with the complementary polymer, would retain the interferoninducing ability of the poly (I,C) complex. The thermodynamic and optical properties of oligo (I).poly (C) complexes have been described in detail.

the $T_m$ of the oligomer-polymer complex is dependent on the oligomer chainlength and on the concentration of the complexes and is less than that of the polymer-polymer complex. The melting profiles of $r(Ip)_9I \cdot rC_n$ (assayed by absorbance) and of $r(Ip)_{16}I \cdot rC_n$ (assayed by optical rotation) are shown in FIG. 4, and some of the $T_m$ values of the complexes are listed in Table 4. The complexes of $r(I)_{n<10} \cdot rC_n$ have $T_m$ values lower than 37° C; therefore, the lack of biological activity of these complexes (Table 4) is not surprising. In the case of $rC_n \cdot r(Ip)_{16}I$, the incubation temperature during the exposure (1 hr) was reduced to 30° C instead of 37° C (a practice which has been found in our laboratory to have no significant effect so that the oligo I·$rC_n$ complex ($T_m = 47°$ C) could remain helical during the exposure. Under this condition, the biological activity of this oligo I·$rC_n$ complex was found to be only marginal, even at a concentration of $10^{-3}$ M. For the $r(Ip)_{18}I \cdot rC_n$ complex ($T_m \approx 50°$ C), definite indication of biological activity was observed (Table 3), even though it is at least 100-fold less than $rI_n \cdot rC_n$.

$rI_n \cdot rC_n$. The complex with the largest oligomer, $rI_n \cdot r(Cp)_{48}G > p$, has a very high $T_m$ (59.6° C), but is tenfold less active than $rI_n \cdot r(C_{20},G)_n \cdot rI_n \cdot r(Cp)_{23}G > p$ is about tenfold more active than $r(Ip)_{18}I \cdot rC_n \cdot rI_n \cdot (Cp)_{11}G > p$ showed only a small amount of activity, as may be anticipated, since the $T_m$ of this complex is below the 37° C incubation temperature.

Two conclusions can be drawn from the above results. First, interruption of one of the strands in the helical complex definitely reduced the interferon-inducing activity, as exemplified by the comparison between $rI_n \cdot r(C_{20},G)_n$ versus $rI_n \cdot r(Cp)_{48}G > p$ (Table 5). In this case, the $rI_n \cdot (Cp)_{48}G > p$ has almost the same $T_m$ (59.6°

Table 4

Antiviral resistance by oligo I.$rC_n$ complexes

| Inducer | $T_m$ (° C) | Concn, (of mononucleotides) (M) | Interference Intracellular protection, % Exp. A | Exp. B | Virus yield Exp. A | Exp. B | Interferon (units/ml.) |
|---|---|---|---|---|---|---|---|
| $rC_n \cdot r(Ip)_2I$ | <0 | 1 × 10$^{-4}$ | 8 | — | — | — | 0 |
| $rC_n \cdot r(Ip)_5I$ | <0 | 1 × 10$^{-4}$ | 14 | — | 1.0 × 10$^9$ | — | 0 |
|  | 7.0 | 1 × 10$^{-3}$ | 18 | — | 3.0 × 10$^9$ | — | 0 |
| $rC_n \cdot r(Ip)_9I$ | 20.5 | 1 × 10$^{-3}$ | 11 | — | 1.0 × 10$^8$ | — | — |
| $rC_n \cdot r(Ip)_{12}I$ | 45.0 | 2 × 10$^{-5}$ | 10 | — | 1.0 × 10$^9$ | — | — |
|  |  | (I : I poly L-lysine) |  |  |  |  |  |
| $rC_n \cdot r(Ip)_{16}I^+$ | 47.0 | 1 × 10$^{-3}$ | 10 | 28 | — | 2.5 × 10$^8$ | — |
| $rC_n \cdot r(Ip)_{10}I$ | <50.0 | 1 × 10$^{-3}$ | — | 26 | — | 5.1 × 10$^7$ | — |
| $rI_n \cdot rC_n$ |  | 1 × 10$^{-4}$ | 100 | — | 3.0 × 10$^2$ | — | 25 |
| $rI_n \cdot rC_n^+$ |  | 1 × 10$^{-4}$ | 100 — | 3.0 × 10$^2$ | — | 25 | — |
| $rI_n \cdot rC_n$ |  | 1 × 10$^{-5}$ | 100 | 39 | 1.2 × 10$^4$ | 2.4 × 10$^7$ | — |
| None |  |  | 10 | 13 | 1.0 × 10$^9$ | 6.6 × 10$^6$ | 0 |

Complexes were exposed to cells at 4° C for 60 min in standard buffer, except as indicated (+).
+Complexes were exposed at 30° C for 60 min in a Mg-containing buffer (0.15 NaCl, 0.01 m-MgCl$_2$, 0.01 m-sodium phosphate (pH 7.4).

Figure 5:
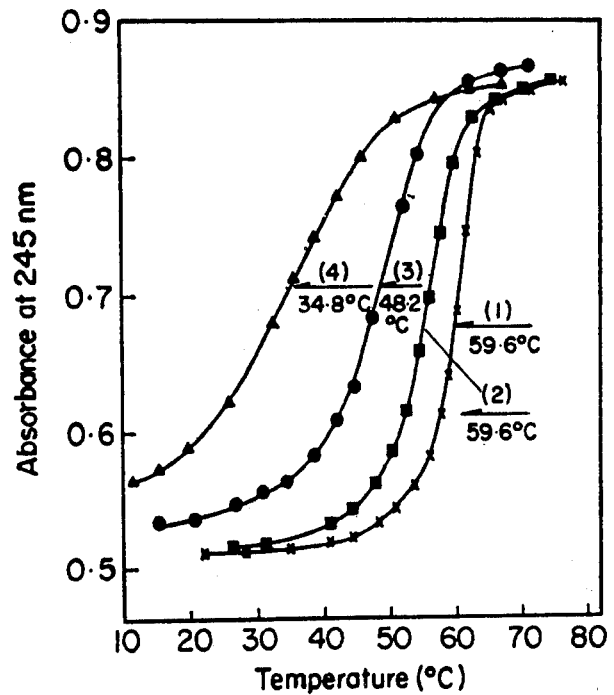
FIG. 5 is a graphic illustration of melting curves of (1) $rI_n \cdot r(Cp)_{48}G > p$, (2) $rI_n \cdot r(Cp)_{35}G > p$, (3) $rI_n \cdot r(Cp)_{23}G > p$, and (4) $rI_n \cdot r(Cp)_{11}G > p$, in minimal Eagle's salt solution, nucleotide concentration being 1 × $10^{-4}M$ in I + C.

The interruption of the $rC_n$ strand was carried out by co-polymerization of GMP into $rC_n$, followed by the RNase T$_1$ enzyme degradation. The G residues serve both as vulnerable positions for specific hyrolysis and as identification of chain-length, since the end residues in all the oligomers are the G residue. Therefore, the $rI_n \cdot r(Cp)_xG > p$ complexes not only have a strand interruption but also a loopingout of the G residue at every interruption. The melting profiles of all the $rI_n \cdot r(Cp_xG > p$ complexes are shown in FIG. 5. The $rI_n \cdot$oligo C complexes do have lower $T_m$ values than the $rC_n \cdot$oligo 1 with oligomer of the same chain length. Therefore, in terms of thermal stability, $rI_n \cdot r(Cp)_nG > p$ is approximately equivalent to $r(Ip)_{18}I \cdot rC_n$ under similar conditions. The biological activities of these $rI_n \cdot r(Cp)_iG > p$ complexes are lower than the original $rI_n \cdot r(C_{20},G)_n$ complex which is almost the same as the C) as that of $rI_n \cdot r(C_{20},G)_n$ (60.9° C) and the $rI_n \cdot r(Cp)_{48}G > p$ contains even less frequency of unpaired G; yet the biological activity of $rI_n \cdot r(Cp)_{48}G > p$ is tenfold less than that of the uninterrupted $rI_n \cdot r(C_{20},G)_n$. Second, the $rI_n \cdot$oligo C complex is more biologically active than the oligo I·$rC_n$ complex, even when they are similar in thermal stability and not greated different in oligomer chain length. This is illustrated in the comparison between $rI_n \cdot r(Cp)_{23}G > p$ versus $r(Ip)_{18} \cdot I \cdot rC_n$, in which the former complex is tenfold more active than the latter. This observation reinforces the conclusion that modification on the $rI_n$ strand has a larger biological effect than that on the $rC_n$ strand.

Table 5

| Inducer | Concentration (M) | Antiviral resistance by $rI_n$ . oligocytidylate complexes Intracellular protection (%) | Virus yield | Interferon yield (units) |
|---|---|---|---|---|
| $rI_n \cdot r(C_{20},G)_n$ | 1 × 10$^{-3}$ | 100 | 2.4 × 10$^5$ | — |
| $rI_n \cdot r(C_{20},G)_n$ | 1 × 10$^{-4}$ | 100 | 7.2 × 10$^6$ | 5 |
| $rI_n \cdot r(C_{20},G)_n$ | 1 × 10$^{-5}$ | 98(81) | 1.2 × 10$^8$ (1.1 × 10$^6$) | <5 (>5) |
| $rI_n \cdot r(Cp)_{40}G > p$ | 1 × 10$^{-3}$ | 100 | — | 20 |
| $rI_n \cdot r(Cp)_{40}G > p$ | 1 × 10$^{-4}$ | 100 | — | 5 |
| $rI_n \cdot r(Cp)_{40}G > p$ | 1 × 10$^{-5}$ | 12 | — | — |
| $rI_n \cdot r(Cp)_{35}G > P$ | 1 × 10$^{-3}$ | 100 | 6.9 × 10$^5$ | 5 |
| $rI_n \cdot r(Cp)_{35}G \times p$ | 1 × 10$^{-4}$ | 100 | 2.7 × 10$^7$ | <5 |
| $rI_n \cdot r(Cp)_{35}G > P$ | 1 × 10$^{-5}$ | 10 | 1.2 × 10$^{10}$ | — |
| $rI_n \cdot (Cp)_{35}G > p$ | 1 × 10$^{-5}$ (1 : 1 poly-L-lysino) | — | 7.5 × 10$^9$ | — |
| $rI_n \cdot r(Cp)_{23}G > p$ | 1 × 10$^{-3}$ | 85(92) | 1.5 × 10$^8$(1.7 × 10$^5$) | <3 |
| $rI_n \cdot r(Cp)_{23}G > p$. | 7 1 × 10$^{-4}$ | 9.0 × 10$^9$ | — |  |
| $rI_n \cdot r(Cp)_{23}G > p$ | 1 × 10$^{-5}$ | — | 3.3 × 10$^9$ | — |
| $rI_n \cdot r(Cp)_{23}G > p$ | 1 × 10$^{-5}$ (1 : 1 poly-L-lysino) | 6 | — | — |
| $rI_n \cdot r(Cp)_{11}G > p$ | 1 × 10$^{-3}$ | 21 | — | 0 |
| $rI_n \cdot r(Cp)_{11}G > p$ | 1 × 10$^{-4}$ | 7 | — | — |
| $rI_n \cdot r(Cp)_{11}G > P$ | 1 × 10$^{-5}$ | 6 | — | — |
| Viral control |  | 6 | 1.3 × 10$^{10}$ (6.6 × 10$^6$) | 0 |
| $r(I_m \cdot r(C)_n$ | 1 × 10$^{-5}$ | 100(40) | —(2.4 × 10$^7$) | 10 (>5) |

Sensitivity of the modified $rI_n \cdot rC_n$ complexes and the properties of ternary complexes of $rI_n \cdot rC_n$ (both modified and unmodified) with polylsine (both D and L-forms)

The above modifications introduced to the $rI_n \cdot rC_n$ complex (mismatching and interruption) invariably led to a loss of biological activity in varying degrees. Before this observation can be interpreted properly, we should be certain that this loss of biological activity is not simply a reflection of the increase in sensitivity of these modified complexes to attack of nucleases. As indicated in FIGS. 6 and 7, the biologically inactive $r(I_{21},u) \cdot rC_n$ and $rI_n \cdot r(C_4,U)_n$, as well as the less active $rI_n \cdot r(Cp)_{48}g > p$, are considerably more sensitive to attack of pancreatic RNase A than the highly active $rI_n \cdot rC_n$.

One known procedure to protect RNA from nuclcases is by complex formation with a polycation. Interaction of poly-L-lysine with $rI_n \cdot rC_n$ was first investigated by Tsuboi, Matsuo & Ts'0 (1966); they reported a stoichiometry of 1 lysine : 2 nucleotides in a solution of dilute salt (0.05 M-NaCl, 0.001 M-sodium citrate, pH 7.0). This stiochiometry was reflected by the proportionality of a two-step melting profile, lower transition (57° C) for the uncomplexed $rI_a \cdot rC_n$ and a higher transition (~90° C) for the ternary poly-L-lysine + $rI_n \cdot rC_n$ complex.

It has been shown that the binding of poly-L-lysine to RNA (1 mg/ml.) on an equivalent bases resulted in the formation of insoluble complexes at low salt concentration. Soluble complexes are formed, however, at a low poly-L-lysine/RNA ratio. Digestion of the soluble complexes by pancreatic ribonuclease, ribonuclease $T_1$, non-specific ribonuclease from *Bacillus cereus*, and Micrococcal nuclease yielded a precipitate with a lysine/-nucleotide ratio of 1:1. Together with other supporting experiments it was concluded that the complex formation between RNA and poly-L-lysine protected the RNA from attack by these nucleases. Our recent reinvestigation of this interaction showed that, in Eagle's salt solution (0.15 M-NaCl, 0.001 M-MgCl$_2$ and 0.01 M-PO$_4$, pH 7.2), the stoichiometry of the ternary complex of poly-L-lysine to $rI_n \cdot rC_n$ is lysine : 1 nucleotide, instead of 1:2 observed earlier in dilute salt, A two-step transition profile was observed in solutions with poly-L-lysine present in less than 1:1 stoichiometry. The $T_m$ of the ternary complex is about 83±1 deg. C. At a low concentration of $rI_n \cdot rC_n$ (less than $5 \times 10^{-5}$M), by adding an equal volume of nucleic acid solution slowly with mixing to a poly-L-lysine solution at room temperature, precipitation can be kept to a minimum (less than 10%). However, such a solution invariably became cloudy at elevated temperature, especially near the $T_m$. This phenomenon, the precipitation of the melted complex in the presence of poly-L-lysine, was verified by the observation that the single stranded $rI_n$ and $rC_n$ are much less soluble than the double-stranded complex ($rI_n \cdot rC_n$) in the presence of poly-L-lysine. We also have investigated the formation of $rI_n \cdot rC_n$ with poly-D-lysine. Many properties of this ternary complex are similar to those of poly-L-lysine, except that the $T_m$ of this ternary complex is only about 68° C.

Figure 6:
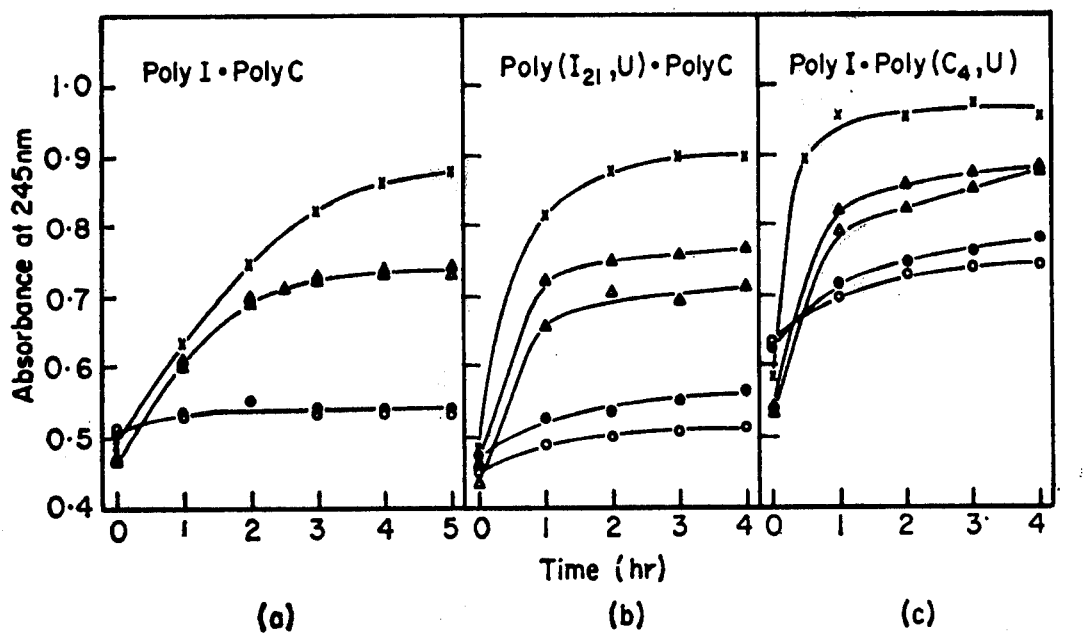
FIG. 6 is a graphic illustration of the hydrolysis by pancrease RNase of (a) $rI_n \cdot rO_n$, (b) $r(I_{21}, U_{,n} \cdot rC_n$, (c) $rI_n \cdot r(C_4,U)_n$ and their complexes with poly-L-lysine and poly-D-lysine, the polynucleotide complex alone being represented by the line X—X, its complex with poly-L-lysine by the line Δ—Δ (P/N ratio = 2) and O—O (P/N ratio = 1), its complex with poly-D-lysine by the line ▲-▲ (P/N ratio = 2) and ●-● (P/N ratio = 1)
Figure 7:
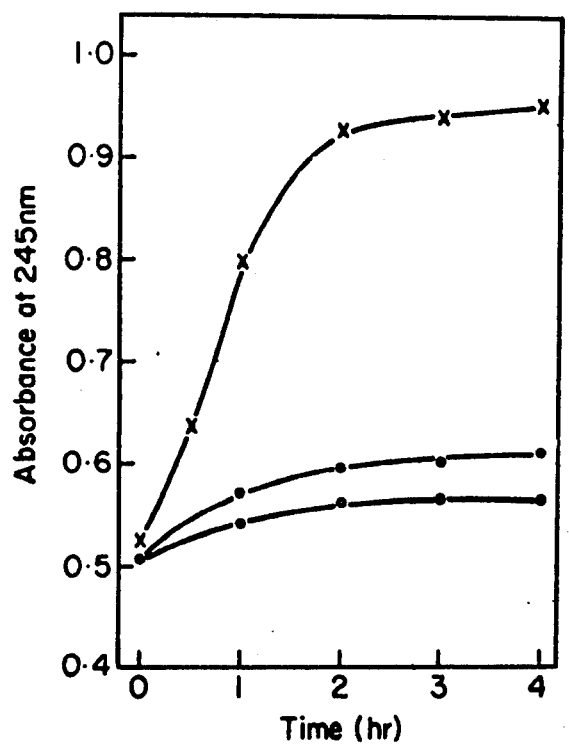
FIG. 7 is a graphic illustration of the hydrolysis by pancrease RNase of $rI_n \cdot r(Cp)_{48}G > p$, the polynucleotide complex alone being represented by the line X—X, its complex with poly-L-lysine by the line ●-● (P/N ration = 1), in minimal Eagle's salt solution, nucleotide concentration being $1 \times 10^{-5}M$ in I + C; and, FIG. 8 is a graphic illustration of the hydrolysis of $r(I)_n \cdot r(C)_n$, represented by the line ▲-▲, $r(I)_n$, represented by the line O—O, and $r(I)_n \cdot r(C_{20}, G)_n$, represented by the line ●-●, with 5μg/ml. of RNase $T_1$ and pancreatic RNase A at 37° C in Eagle's medium.

As shown in FIGS. 6 and 7, in the ternary complex with either poly-L-lysine or poly-D-lysine in a 1:1 ratio (N/P), the modified or unmodified $rI_n \cdot rC_n$ complex was mostly protected from the pancreatic RNase. Interestingly, in the complex with a 1 lysine: 2 nucleotide ratio, merely half of the polynucleotide complexes were protected. This observation confirmed the 1:1 stoichiometry of these ternary complexes.

Table 6 shows that poly-L-lysine alone does not prevent the multiplication of bovine vesicular stomatitis virus. Ternary complex of $rI_n \cdot rC_n$ with poly-L-lysine in 1:0.5 (P/N) ratio, 1:1 ratio, and 1:5 ratio, all have about the same biological activity as the uncomplexed $rI_n \cdot rC_n$. Complex formation with poly-L-lysine, however, does not significantly enhance the activity of $rI_n \cdot rC_n$ either, when $rI_n \cdot rC_{n\ was\ supplied\ in\ suboptimal\ concentration}$ ($1 \times 10^{-6}$ M. Table 7).

TABLE 6

| | | | | Interference induced by $rI_n \cdot rC_n$ . lysine complexes | | |
|---|---|---|---|---|---|---|
| | | | | | Interference | |
| Inducer[+] | (M) | Polycation | (M) | P/N ratio | Intracellular protection, % | Virus yield |
| $rI_n \cdot rC_n$ | $5 \times 10^{-6}$ | poly-L-lysino | $2.5 \times 10^{-6}$ | 1:0.5 | 100 | — |
| $rI_n \cdot rC_n$ | $5 \times 10^{-6}$ | poly-L-lysino | $5.0 \times 10^{-6}$ | 1:1 | 100 | $4 \times 10^3$ |
| $rI_n \cdot rC_n$ | $5 \times 10^{-6}$ | poly-L-lysino | $2.5 \times 10^{-5}$ | 1:5 | 100 | — |
| $rI_n \cdot rC_n$ | $5 \times 10^{-6}$ | None | | — | 100 | $5 \times 10^3$ |
| None | | poly-L-lysine | $2.5 \times 10^{-6}$ | — | 11 | $2 \times 10^5$ |
| None | | poly-L-lysine | $5.0 \times 10^{-6}$ | — | 12 | $2 \times 10^5$ |
| None | | poly-L-lysine | $2.5 \times 10^{-5}$ | — | 11 | $2 \times 10^5$ |
| None | | None | | — | 10 | $1 \times 10^6$ |

+All exposures were for 60 min at 37° C.

Results given in Tables 4, 5 and 7 show that in the ternary complex formation with either poly-L-lysine or poly-D-lysine, in 1:1 ratio or 2:1 ratio (N/P), the interferon-inducing activity of the modified $rI_n \cdot rC_n$ complexes has not been increased. For example, though the susceptibility to nucleases of $r(I_{21},U)_n \cdot rC_n$ and $rI_n \cdot rC_{4,u)_n}$ are greatly reduced by complex formation with poly-L-lysine (FIG. 5), the biological activities of these inactive, modified complexes were not enhanced (Table 7). Similarly, the activities of the moderately active $rI_n \cdot r(Cp)_{35}G > p$ and $rI_n \cdot r(Cp)_{23}G > p$ were not promoted by formation of a 1:1 complex with poly-L-lysine (Table 5), even though this ternary complex should have reduced the susceptibility of the polynucleotides to nucleases, as extrapolated from the results on $rI_n \cdot r(Cp)_{48}G$(FIG. 7). In addition, tho $T_m$ of the $rC_n \cdot r(I_p)_{12}I$ has been increased to 45° C, significantly above the incubation temperature, by complex formation with poly-L-lysine, and this $rC_n \cdot$oligo I complex remained inactive (Table 4). Therefore, the reduction of susceptibility to nucleases and the enhancement in $T_m$ brought about by the ternary complex with polylysine (L or D) did not transform the inactive, modified $rI_n \cdot rC_n$ complexes into an active state.

more susceptible to nucleases. In addition, ternary complex formation with polysine (both L and D forms) virtually protected all these polynucleotide helices from nuclease, yet their biological activities were not

TABLE 7

Interference induced by complexes of $rI_n \cdot rC_n$ (containing non-base-paired regions) with polysine

| Inducer | Concn (M) | Polycation | P/N ratio | Intracellular protection Exp. A | Intracellular protection Exp. B | Virus Exp. B |
|---|---|---|---|---|---|---|
| $rI_n \cdot rC_n$ | $10^{-6}$ | — | — | 93 | — | $1.1 \times 10^6$ |
| $rI_n \cdot rC_n$ | $10^{-5}$ | D-lysino | 2:1 | 96 | — | — |
| $rI_n \cdot rC_n$ | $10^{-5}$ | L-lysino | 2:1 | 92 | — | — |
| $rI_n \cdot rC_n$ | $10^{-6}$ | — | — | — | 10 | $7.8 \times 10^9$ |
| $rI_n \cdot rC_n$ | $10^{-6}$ | L-lysino | 1:1 | — | 13 | $3.3 \times 10^9$ |
| $r(I_{39},U) \cdot rC_n$ | $10^{-5}$ | — | — | — | 7 | $6.9 \times 10^9$ |
| $r(I_{39},U) \cdot rC_n$ | $10^{-5}$ | L-lysino | 1:1 | — | 12 | $9.6 \times 10^9$ |
| $r(I_{19},U) \cdot rC_n$ | $10^{-5}$ | — | — | — | 7 | $3.3 \times 10^9$ |
| $r(I_{19},U) \cdot rC_rC_n$ | $10^{-5}$ | L-lysino | 1:1 | — | 13 | $6.0 \times 10^9$ |
| $r(I_{19},U) \cdot rC_n$ | $10^{-5}$ | L-lysino | 2:1 | 10 | — | — |
| $r(I_{19},U) \cdot rC_n$ | $10^{-5}$ | D-lysino | 2:1 | 10 | — | — |
| $rI_n \cdot r(C_7,U)$ | $10^{-5}$ | — | — | — | 21 | $1.0 \times 10^9$ |
| $rI_n \cdot r(C_7,U)$ | $10^{-5}$ | L-lysino | 1:1 | — | 27 | $3.2 \times 10^9$ |
| $rI_n \cdot r(C_7,U)$ | $10^{-5}$ | L-lysino | 2:1 | 34 | — | — |
| $rI_n \cdot r(C_7,U)$ | $10^{-5}$ | D-lysino | 2:1 | 29 | — | — |
| $rI_n \cdot r(C_4,U)$ | $10^{-5}$ | — | — | — | 30 | — |
| $rI_n 19 \ r(C_4,U)$ | $10^{-5}$ | L-lysino | 2:1 | 32 | — | — |
| $rI_n \cdot r(C_4,U)$ | $10^{-5}$ | D-lysine | 2:1 | 34 | — | — |
| Viral control | — | — | — | 6 | 15 | $3.3 \times 10^9$ |

Relative rates of enzymic hydrolysis of several complexes with similar interferon inducing activities As described in Tables 3 and 5, $rI_n \cdot r(C_{13},U)_n$ and $rI_n \cdot rC_{20},G)_n$ are essentially as active in interferon induction as unmodified $rI_n \cdot rC_n$. It is of both theoretical and practical interest to compare the susceptibility of these complexes toward nucleases. Tho $T_1$ ribonuclease, an endonuclease for the $rI_n$ strand and G residue, and the pancreatic RNase A, an endonuclease for the $rC_n$ strand, were both used in this experiment.

Figure 8:
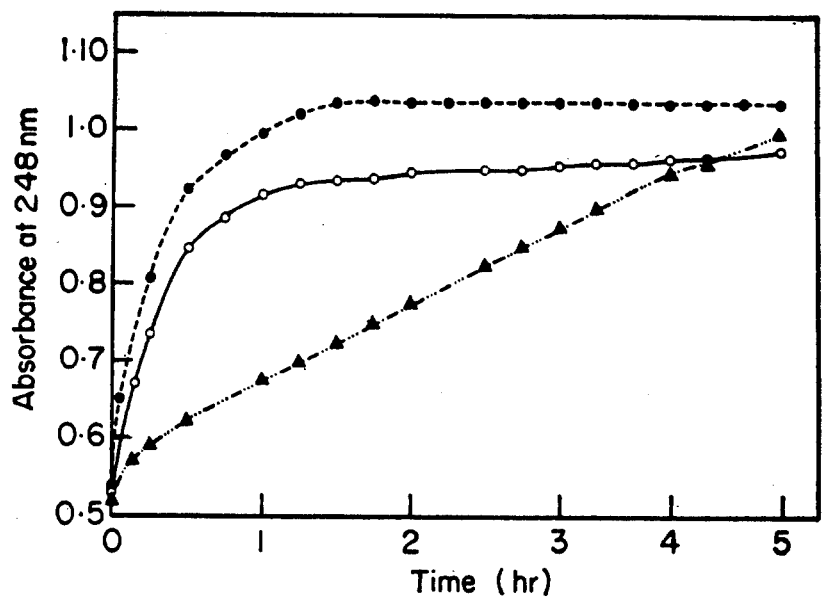

The data in FIG. 8 clearly show that both modified complexes were hydrolyzed at rates of 5- to 8-fold more rapidly than $rI_n \cdot rC_n$; indeed, approximately 50% of their total hydrolysis occurred within the first 12 minutes of incubation. Previous work has suggested that high antiviral activity of synthetic polynucleotide inducers is integrally associated with their prolonged stability in biological fluids; and, as greater antiviral activities are achieved further toxicities simultaneously accrue.

It has been found that it is possible to prepare a polynucleotide complex which is highly active as an interferon inducer but also highly susceptible to neclease.

Two types of structural modifications were made to the $rI_n \cdot rC_n$ complex in this investigation: (1) Mismatching of bases, which cause a looping-out from the helix; and (2) strand interruption. The interferon-inducing activity of $rI_n \cdot rC_n$ is lowered by these modifications in varying degrees; the decrease is much more significant when the perturbation is imposed upon the $rI_n$ strand than upon the $rC_n$ strand. This lowering of the biological activity of $rI_n \cdot rC_n$ cannot be explained by the two simple requirements for thermal stability, and susceptibility to nucleases. The $T_m$ values of the modified $rI_n \cdot rC_n$ complexes are only slightly less than that of $rI_n \cdot rC_n$ and are well above the incubation temperature of the cells. Ternary complex formation with poly-L-lysine significantly increases the $T_m$ of these polynucleotide helices, but has little effect on their biological activities. These modified complexes are more susceptible to nucleases: however, modified $rI_n \cdot rC_n$ complexes can be prepared which have biological activities comparable to those of the original $rI_n \cdot rC_n$, but are much changed significantly. These observations and reasonings indicate that the structural modifications introduced here may be directly related to the structural requirement of receptors in the cells responsible for the triggering mechanism of interferon production.

The apparently stringent requirement for the polynucleotide complex in order to be an effective interferon inducer is well known. However, it has been reported that ternary complex formation with DEAE-dextran significantly enhanced the biological activity of $rI_n \cdot rC_n$.

Most of the effect was attributed by the investigators to an increase of uptake and protection from endonucleases. It has been proposed that the change of mass to charge ratio may facilitate the uptake process, which is part of the consideration related to the question of specificity. However, the fate of such a complex inside the cell has not been discussed. It is not known in what manner the DEAE-dextran can be dissociated from the $rI_n \cdot rC_n$ complex or can be degraded. Similarly, in this investigation, ternary complex formation with polylysine (both L and D), did not change the biological activity of $rI_n \cdot rC_n$ as interferon inducer. A relevant study on the physico-chemical properties of DNA, RNA, $rA_n \cdot rU_n$ and $rI_n \cdot rC_n$ upon complex formation has been reported. The circular dichroism spectrum of $rI_n \cdot rC_n$ has been drastically changed upon complex formation with poly-L-lysine and the ternary complex has also been investigated by high-angle X-ray diffraction, low-angle X-ray diffraction and by electron microscopy. While definite information about the helical structure cannot yet be obtained, it is most likely that the ternary complex is a multiple-stranded fiber. It has also been reported that the infectious RNA of two equine encephalitis viruses lost their infectivity upon complex formation with poly-L-lysine, though the activity of such a complex can be recovered after pronase treatment or dissociation by strong salt. This polylysine-RNA complex was resistant to inactivation of the nuclease.

At present, we have no knowledge about the fate of the polysine-$rI_n \cdot rC_n$ complex outside the cell during the incubation period of one hour, or of the complex remaining within the cell at the end of exposure after washing. It does not appear to be a simple, easy process for the removal of polylysine from the ternary complex, either by dissociation or by degradation (especially the D-analog). It remains a possibility that the "receptors" in the cell can be triggered by the entire ternary complex containing both polylysine and $rI_n \cdot rC_n$. However, as described above, the conformation of $rI_n \cdot rC_n$ has been greatly changed by the association with polylysine.

Analysis of the composition revealed that the actual synthesis produced polymers which have about one half as much as the 2'-O-Methylinosinic originally put into the reaction mixture. For example, in the composition given in Tables VIII and IX, these compositions were given, as indicated in the footnotes of those tables, as an input concentration into the enzyme mixture during the preparation procedure but the analysis of the result indicates the amount of mI is only half of that put in. Therefore, the correct chemical composition, in the cases determined, always contains half of the mI as put into the original enzyme mixture. For example, $rI_{10}$,mI which is now cited in Table VIII represents the input ratio. The chemical ratio of the product actually is $rI_{20}$,mI, which is footnoted in Table VIII.

A biological activity of poly 2'-O-Methylinosinic as well as the hybrid strands containing both iosinic residue and 2'-O-Methlinosinic residue were tested on human cells. These compounds first will form complex with rC polyribocytidylic in a manner described in the experiments. The results indicate clearly that the poly 2'-O-Methylinosinic polyribocytidylic 1 to 1 complex has little or no activities as human cells interferon inducer as compared to the original rI·rC. However, in the case of the hybrid molecules, the results are totally different. As recorded in Tables VIII and IX, the human cells and cultures respond to the complex rC as well as the hybrid molecules of polyinosine and 2'-O-Me inosine produce significantly much better results in tests against viral attacks as compared to the original rI·rC. It is to be noted from the footnotes of Tables VIII and IX that the composition of the products are certainly not identical to the input of the original substrates in the enzyme preparation.

It can be summarized from Tables VIII and IX that 1 to 1 complex of rC and polyinosinic containing 5 to 16% 2'-O-Me inosine can be 100 fold more as effective as rI·rC in inducing interferons from human cells. This is a very important finding, perhaps allowing the administration of the drug a hundred fold less in a dose level producing the therapeutic value.

TABLE 8

Interference induced by $(rI_{10-40},mI)_n \cdot rC_n$ as compared to those induced by $rI_n \cdot rC_n$*

| | Conc. | Intracellular Protection (%) | Reduction of Virus Yield |
|---|---|---|---|
| $rI_n \cdot n$ | I = 5 × 10$^{-4}$ M | 100 | 8.2 × 10$^6$ |
| | II = 1 × 10$^{-5}$ M | 44 | 3.1 × 10$^4$ |
| | III = 5 × 10$^{-5}$ M | 0 | 5.1 × 10$^3$ |
| $(rI_{40},mI)_n \cdot rC_n$ | I | 100 | 1.5 × 10$^7$ |
| | II | 15 | 7.2 × 10$^4$ |
| | III | 0 | 4.2 × 10$^3$ |
| $(rI_{20},mI)_n \cdot rC_n$ | I | 100 | 1.8 × 10$^6$ |
| | II | 34 | 1.1 × 10$^4$ |
| | III | 0 | 2.3 × 10$^3$ |
| $(rI_{10},mI)_n \cdot rC_n$ | I | 100 | 2.5 × 10$^6$ |
| | II | 68 | 3.1 × 10$^7$ |
| | III | 60 | 9.0 × 10$^6$ |

*The ratio of the composition of the hypoxanthine polynucleotide is the input ratio of the Inosine 5'-diphosphate/2'-O-Me inosine 5'-diphosphate in the enzyme procedure for the synthesis. The actual ratio of the chemical composition of the product usually contains half as much as 2'-O-Me inosine residue in the strand as the input ratio to the preparation. For example, $(rI_{10},mI)_n$ (input ratio) ≈ $(rI_{20},mI)_n$ (product ratio).

TABLE 9

Interference induced by $(rI_{25-40},mI)_n \cdot rI_n$ is compared to those induced by $rI_n \cdot rI_n$*

| | Conc. | Intracellular Protection % | Reduction of Virus Yield | Interferon units/ml |
|---|---|---|---|---|
| $rI_n \cdot rC_n$ | I = 1 × 10$^{-4}$M | 94 | 3 + 10$^3$ | 48 |
| | II = 1 × 10$^{-5}$M | 88 | — | — |
| | III = 1 × 10$^{-6}$M | 0 | 1.8 × 10$^1$ | <8 |
| $(rI_{40},mI)_n \cdot rC_n$ | I | 90 | 3.9 × 10$^3$ | 84 |
| | II | 89 | — | — |
| | III | 0 | 1.5 × 10$^1$ | <8 |
| $(rI_{20},mI)_n \cdot rC_n$ | I | 100 | 2.3 × 10$^3$ | 52 |
| | II | 40 | — | — |
| | III | 0 | 1.2 × 10$^1$ | <8 |
| $(rI_{10},mI)_n \cdot rC_n$ (#1) | I | 96 | 4.4 × 10$^3$ | 54 |
| | II | 96 | — | — |
| | III | 73 | 4.2 × 10$^1$ | <8 |
| $(rI_{10},mI)_n \cdot rC_n$ (#2) | I | 96 | 6.1 × 10$^3$ | 62 |
| | II | — | — | — |
| | III | 96 | 1 × 10$^4$ | 18 |
| $(rI_5,mI)_n \cdot rC_n$ | I | 100 | 6.1 × 10$^3$ | 6 |
| | II | — | — | — |
| | III | 100 | 4.6 × 10$^3$ | 9 |
| $(rI_{2.5},mI)_n \cdot rC_n$ | I | 95 | 3.9 × 10$^3$ | 38 |
| | II | = | = | = |
| | III | 86 | 4.1 × 10$^3$ | 13 |

*The ratio of the composition of the hypoxanthine polynucleotide is the input ratio of Inosine 5'-diphosphate/2'-O-Me inosine 5'-diphosphate in the enzyme procedure for the synthesis. The actual ratio of the chemical composition of the product usually contains half as much as 2'-O-Me inosine residue in the strand as the input ratio to the preparation. For example, $(rI_{10},mI)_n$ (input ratio) ≈ $(rI_{20},mI)_n$ (product ratio)

What is claimed is:

1. A method for inducing interferon production in living animal cells in culture without toxic effects to the cells, comprising the step of:
administering an effective amount of a double-stranded, helical RNA molecular species having at least one chemical site which is readily hydrolyzed by nucleases, said site being created by the incorporation into the RNA strand of an unpaired nucleotide such as guanine nucleotide and uridine nucleotide wherein said nucleotide contains a 3'-connected to 5'-phosphoryl diester linkage.

2. The method of claim 1 wherein said helical RNA molecular species is $rI_n \cdot rC_n$.

3. The method of claim 1 wherein said molecular species comprises $rI_n \cdot rC_n$ having a methyl group bonded thereto.

4. The method of claim 1 wherein said molecular species is selected from the group consisting of the $(rI_{5-20}, mI)_n \cdot rC_n$ complexes wherein m is the 2'-O-Methyl ribosyl group and the polyinosinate strand consists of 5–16% 2'-O-Methylinosine residue.

5. A method of therapeutically inducing interferon production in a human in need of such therapy, which method comprises:

administering to the human an effective amount of a complex selected from the group consisting of $poly(I) \cdot poly(C_n, U)$ and $poly(I) \cdot poly(C_n, G)$, wherein n is an integer having a value of from 4 to 29 to induce interferon.

6. A method as in claim 5 wherein the complex is $poly(I) \cdot poly(C_4, U)$.

7. A method as in claim 5, wherein the complex is $poly(I) \cdot poly(C_7, U)$.

8. A method as in claim 5, wherein the complex is $poly(I) \cdot poly(C_{13}, U)$.

9. A method as in claim 5, wherein the complex is $poly(I) \cdot poly(C_{22}, U)$.

10. A method as in claim 5, wherein the complex is $poly(I) \cdot poly(C_{20}, G)$.

11. A method as in claim 5, wherein the complex is $poly(I) \cdot poly(C_{29}, G)$.

* * * * *

UNITED STATES PATENT AND TRADEMARK OFFICE
CERTIFICATE OF CORRECTION

PATENT NO. : 4,130,641
DATED : December 19, 1978
INVENTOR(S) : Paul O. P. Ts'o; William A. Carter It is certified that error appears in the above-identified patent and that said Letters Patent are hereby corrected as shown below:

Column 1, line 23, "cell" should read --cells--;

line 25, "cell" should read --cells--;

line 46, "necleuses" should read -- nucleases --

Column 3, line 49, "in" should read --is--.

Column 4, line 5, "ration" should read --ratio--.

Column 6, Table 1, in the Table columnar headings, "Sedimentation coefficient $(S_{30,hi}{}^+$" should read --Sedimentation coefficient $(S_{20,w})+$--.

Columns 7, Table 1, in the Table columnar headings, "Sedimentation coefficient $(S_{30,hr}{}^+$" should read --Sedimentation coefficient $(S_{20,w})+$--;

Column 7, Table 1, in the column under 'Polymer', fourth line, "poly $(C_1,U)$" should read --$(C_7,U)$--.

Column 8, Table 2, third column under Column entitled "Guanosine", line 6, "65.7" should read --55.7--;

fifth column under "Average chain

UNITED STATES PATENT AND TRADEMARK OFFICE
CERTIFICATE OF CORRECTION

PATENT NO. : 4,130,641  Page 2 of 8
DATED : December 19, 1978
INVENTOR(S) : Paul O. P. Ts'o; William A. Carter It is certified that error appears in the above-identified patent and that said Letters Patent are hereby corrected as shown below:

length", line 6, "21.1" should read --24.1--.

Columns 9 and 10, Table 3, under the column entitled "Complex+", line 16, "$rI_n \cdot r(C_{22},U)_6$" should read --$rI_n \cdot r(C_{22},U)_n$--;

under the column entitled "Concn.(of mononucleotides (M)", this column heading should read --Concn. (of mononucleotides)(M)--;

line 16, therebelow "$1 \times 10^{-3}$" should read --$1 \times 10^{-5}$--;

under the column entitled " ,U) protection, %", this heading should read --Intracellular protection, %--; and in this column, line 5, under "Exp.A$^{++}$", "U)$_{45}$" should read --61--;

under column entitled "Exp.B$^{++}$", line 5, "$3.0 \times 10^7$" should read --45--;

line 13, "33" should read --35--;

under column entitled "Interference,

UNITED STATES PATENT AND TRADEMARK OFFICE
CERTIFICATE OF CORRECTION

PATENT NO. : 4,130,641          Page 3 of 8
DATED : December 19, 1978
INVENTOR(S) : Paul O. P. Ts'o; William A. Carter It is certified that error appears in the above-identified patent and that said Letters Patent are hereby corrected as shown below:

Exp. $A^{++}$", line 4, "$6.9 \times 10^6$" should read --$6.9 \times 10^8$--;

line 5, "$7.0 \times 10^9$" should read --$3.0 \times 10^7$--;

line 22 (last line), "$9.0 \times 10^5$" should read --$9.0 \times 10^8$--;

under column entitled "Interference, Virus yield Exp.$B^{++}$", line 7, "$1.0 \times 10^7$" should read --$1.0 \times 10^9$--.

under column entitled "Interference, Virus yield, Exp.$C^{++}$", line 5, "0" should be -- - --;

line 9, "$2.1 \times 10^6$" should read --$2.1 \times 10^8$--; and line 10, "$1.0 \times 10^6$" should read --$1.0 \times 10^3$--;

line 22 (last line), "$6.6 \times 10^5$" should read --$6.6 \times 10^8$--;

under column entitled "Interferon (units/ml.), Exp.$A^{++}$", line 5, "-" should be --0--.

Column 9, line 31, "$rI_n \cdot rC_n r(I_{21},U)_n \cdot rC_n$" should read --$rI_n \cdot rC_n, r(I_{21},U)_n \cdot rC_n$--.

UNITED STATES PATENT AND TRADEMARK OFFICE
CERTIFICATE OF CORRECTION

PATENT NO. : 4,130,641
DATED : December 19, 1978
INVENTOR(S) : Paul O. P. Ts'o; William A. Carter It is certified that error appears in the above-identified patent and that said Letters Patent are hereby corrected as shown below:

line 39, "1 mg/ml; and." should read --1 mg/ml; 60µl.--.

Column 12, line 47, "OLigo" should read --Oligo--;

line 52, delete "(I)poly";

line 61, "the" (first occurrence) should be --The--.

Column 13, line 10, "M" should be --m--.

Column 13, Table 4, under the column entitled "Intracellular protection, %, Exp.A", line 11, after "100" delete the dashes(=); under "Exp.B", line 10, delete "$3.0 \times 10^2$".

Column 14, line 13, "$rI_n \cdot (Cp)_{48}G \rangle p$" should read --$rI_n \cdot r(Cp)_{48}G \rangle p$--;

line 37, "greated" should read --greatly--.

UNITED STATES PATENT AND TRADEMARK OFFICE
CERTIFICATE OF CORRECTION

PATENT NO. : 4,130,641

DATED : December 19, 1978

INVENTOR(S) : Paul O. P. Ts'o; William A. Carter

Page 5 of 8

It is certified that error appears in the above-identified patent and that said Letters Patent are hereby corrected as shown below:

Column 14, Table 5, in the column entitled "Inducer", line 13, delete "$1 \times 10^{-4}$"; (See below - bottom of page)***** under column entitled "Concentration (M)", line 12, delete "7" and insert -- $1 \times 10^{-4}$ --.

under column entitled "Intracellular protection (%)", line 12, "$9.0 \times 10^9$" should read --7--;

under column entitled "Virus yield", line 3, "$1.2 \times 10^8 (1.1 \times 10^6)$" should read --$1.2 \times 10^8 (1.1 \times 10^6)$--;

line 12, insert --$9.0 \times 10^9$--;

line 13, (next to last line), "$1.3 \times 10^{10} (6.6 \times 10^6)$" should read --$1.3 \times 10^{10} (6.6 \times 10^8)$--.

***** under column "Inducer" lines 4, 5, and 6 "$rI_n \cdot r(Cp)_{40} G>p$", should read --$rI_n \cdot r(Cp)_{48} G>p$--, in each line.

UNITED STATES PATENT AND TRADEMARK OFFICE
CERTIFICATE OF CORRECTION

PATENT NO. : 4,130,641

DATED : December 19, 1978

INVENTOR(S) : Paul O. P. Ts'o; William A. Carter

It is certified that error appears in the above-identified patent and that said Letters Patent are hereby corrected as shown below:

Column 15, line 21, "Ts'O" should read --Ts'o--.

Column 16, Table 6, in the last column entitled "Interference, Virus yield", line 5, "$2 \times 10^5$" should be --$2 \times 10^8$--;

line 6, "$2 \times 10^5$" should be --$2 \times 10^8$--;

line 7, "$2 \times 10^5$" should be --$2 \times 10^8$--; and line 8, "$1 \times 10^6$ should be --$1 \times 10^8$--;

line 64, "tho" should be --the--.

Column 17, Table 7, in the column entitled "Inducer", line 6, "$r(I_{39}, U \cdot) rC_n$" should be --$r(I_{39}, U) \cdot rC_n$--;

line 7, "$r(I_{39}, U \cdot) rC_n$" should be --$r(I_{39}, U) \cdot rC_n$--;

line 17, "$rI_n 19 r(C_4, U)$" should be --$rI_n \cdot r(C_4, U)$--;

in the column entitled "Polycation", delete "2:1";

UNITED STATES PATENT AND TRADEMARK OFFICE
CERTIFICATE OF CORRECTION

PATENT NO. : 4,130,641
DATED : December 19, 1978
INVENTOR(S) : Paul O. P. Ts'o; William A. Carter It is certified that error appears in the above-identified patent and that said Letters Patent are hereby corrected as shown below:

in the column entitled "P/N ratio", line 2, "96" should be --2:1--;

in the column entitled "Intracellular protection, Exp.A", line 2, "-" should be --96--;

in the column entitled "Virus, Exp.B", line 2, the blank space should be -- - --;

line 7, "$9.6 \times 10^9$" should be --$9.6 \times 10^8$--;

line 9, "$6.0 \times 10^9$" should be --$6.0 \times 10^8$--;

line 12, "$1.0 \times 10^9$" should be --$1.0 \times 10^8$--.

Column 20, Table 9, under the three columns entitled "Intracellular Protection %", "Reduction of Virus Yield" and "Interferon units/ml", line 20 of each column, (the next to last line), the "=" should be -- - --.

In the claims:

Claim 4, line 3, "2'-O-" should be --2'-O- --;

line 5, "2'-O-Methylinosine" should be --2-O-Methylinosine--.

UNITED STATES PATENT AND TRADEMARK OFFICE
CERTIFICATE OF CORRECTION

PATENT NO. : 4,130,641

DATED : December 19, 1978

INVENTOR(S) : Paul O. P. Ts'o; William A. Carter

Page 8 of 8

It is certified that error appears in the above—identified patent and that said Letters Patent are hereby corrected as shown below:

On the cover sheet insert -- [73] Assignee: The John Hopkins University, Baltimore, Maryland --.

Signed and Sealed this

Twenty-sixth Day of June 1979

[SEAL]

Attest:

RUTH C. MASON
Attesting Officer

DONALD W. BANNER
Commissioner of Patents and Trademarks